United States Patent [19]

Sarubbi et al.

[11] Patent Number: 5,792,451

[45] Date of Patent: Aug. 11, 1998

[54] ORAL DRUG DELIVERY COMPOSITIONS AND METHODS

[75] Inventors: Donald J. Sarubbi, Bronxville, N.Y.; Andrea Leone-Bay, Ridgefield, Conn.; Duncan R. Paton, Purdys, N.Y.

[73] Assignee: Emisphere Technologies, Inc., Hawthorne, N.Y.

[21] Appl. No.: 205,511

[22] Filed: Mar. 2, 1994

[51] Int. Cl.$^6$ ............................................. A61K 38/21
[52] U.S. Cl. .................... 424/85.4; 424/85.2; 424/141.1; 424/184.1; 424/465; 424/474; 424/489; 424/491; 424/499; 514/2; 514/12; 514/21; 514/773
[58] Field of Search .................... 514/2, 12, 21, 514/773; 424/85.4, 85.2, 141.1, 184.1, 465, 474, 489, 491, 499

[56] References Cited

U.S. PATENT DOCUMENTS

| | | | |
|---|---|---|---|
| Re. 24,899 | 11/1960 | Green | 252/316 |
| 2,671,451 | 3/1954 | Bolger | 128/260 |
| 2,862,918 | 12/1958 | Meyer et al. | 260/123.5 |
| 2,868,740 | 1/1959 | Luce | 260/8 |
| 2,971,916 | 2/1961 | Schleicher et al. | 252/62.5 |
| 3,016,308 | 1/1962 | Macaulay | 177/37 |
| 3,052,655 | 9/1962 | Fox et al. | 260/78 |
| 3,057,344 | 10/1962 | Abella et al. | 128/2 |
| 3,076,790 | 2/1963 | Fox et al. | 260/78 |
| 3,170,802 | 2/1965 | Fukushima | 99/145 |
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato | 424/37 |
| 3,567,650 | 3/1971 | Bakan | 252/316 |
| 3,574,832 | 4/1971 | Engel et al. | 424/183 |
| 3,576,758 | 4/1971 | Emrick | 252/316 |
| 3,687,926 | 8/1972 | Arima et al. | 260/112.5 |
| 3,725,113 | 4/1973 | Chang | 117/82 |
| 3,748,277 | 7/1973 | Wagner | 252/316 |
| 3,794,561 | 2/1974 | Matsukawa et al. | 195/29 R |
| 3,795,739 | 3/1974 | Birkmayer et al. | 424/274 |
| 3,816,404 | 6/1974 | Kablaoui et al. | |
| 3,822,348 | 7/1974 | Higashi et al. | 424/95 |
| 3,849,550 | 11/1974 | Teitelbaum | 424/78 |
| 3,933,873 | 1/1976 | Love et al. | |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |

(List continued on next page.)

FOREIGN PATENT DOCUMENTS

| | | |
|---|---|---|
| 1077842 | 8/1976 | Canada . |
| 0 000 667 A1 | 2/1979 | European Pat. Off. ......... A61K 9/50 |
| 0 036 145 | 9/1981 | European Pat. Off. ......... A61K 31/62 |
| 0 068 314 | 1/1983 | European Pat. Off. . |
| 0 105 804 | 4/1984 | European Pat. Off. ......... C12N 15/00 |
| 0 130 162 A2 | 1/1985 | European Pat. Off. ......... B01J 13/02 |
| 0 170 540 A1 | 2/1986 | European Pat. Off. ......... A61K 9/52 |
| 0 342 054 A2 | 11/1989 | European Pat. Off. ......... A61K 7/06 |
| 0 342 056 A2 | 11/1989 | European Pat. Off. ......... A61K 7/06 |
| 0 365 183 | 4/1990 | European Pat. Off. ......... C07C 311/21 |
| 0 366 277 | 5/1990 | European Pat. Off. ......... A61K 9/107 |
| 0 418 642 | 3/1991 | European Pat. Off. . |
| 0 448 057 | 9/1991 | European Pat. Off. ......... C12P 21/08 |
| 0 452 161 | 10/1991 | European Pat. Off. ......... A61K 7/48 |
| 0 459 795 | 12/1991 | European Pat. Off. ......... A61K 37/02 |
| 0 467 389 | 1/1992 | European Pat. Off. ......... A61K 9/52 |
| 0 490 549 A1 | 6/1992 | European Pat. Off. ......... A61K 47/12 |
| 0 517 211 A1 | 9/1992 | European Pat. Off. ......... A61K 47/12 |
| 0 616 799 A1 | 9/1994 | European Pat. Off. ......... A61K 7/00 |
| 1 351 358 | 3/1964 | France . |
| 1 468 601 | 2/1967 | France . |
| 2 133 926 | 12/1972 | France ......... A61K 27/00 |
| 2 326 934 | 5/1977 | France ......... A61K 47/00 |
| 2 565 102 | 12/1985 | France ......... A61K 9/52 |

(List continued on next page.)

OTHER PUBLICATIONS

Kondo, *Microcapsule Processing and Technology*, pp. 154–165, 1979.
Pastores et al., *Journal of Liquid Chromatography*, 18:3049–3059, 1995.
Sinha et al., *Journal of Biological Chemistry*, 260:10714–10719, 1985.
Franssen et al., *J. Med. Chem.*, 35:1246–1259, 1992.
Chemical Abstracts, 99(23):191473h, Dec. 5, 1983.
Butera et al., *J. Med. Chem.*, 34:3212–3228, 1990.
Cimini et al., *Ann. Rept. in Med. Chem.*, 27:89–98, 1992.
Earley et al., *Brain Research*, 546:282–286, 1991.
Ellingboe et al., *J. Med. Chem.*, 35:705–716, 1992.
Lumma et al., *J. Med. Chem.*, 30:758–763, 1987.
Lynch et al., *J. Pharm. and Exp. Therap.*, 269:541–554, 1994.
Matsuno et al., *Brain Research*, 575:315–319, 1992.
Morgan et al., *J. Med. Chem.*, 33:1091–1097, 1990.
Oinuma et al., *J. Med. Chem.*, 33:903–905, 1990.
Rao et al., *Molecular Pharmacology*, 37:978–982, 1990.
Thompson, Biochem. vol. 12(1), pp. 47–51, 1973.
Thompson et al., *J. Med Chem.*, vol. 29(1), 1986 pp. 104–111 (abstract only).
Douglas et al., *Chemistry and Industry*, 22:748–751, 1985.
Finch, *Chemistry and Industry*, 22:752–756, 1985.
Marie–Claude Fournié–Zulaski et al., "New Carboxyalkyl Inhibitors of Brain Enkephalinase: Synthesis, Biological Activity, and Analgesic Properties", *J. Med. Chem.*, 26, 60–65 (1983).

(List continued on next page.)

*Primary Examiner*—Chhaya D. Sayala
*Attorney, Agent, or Firm*—Darby & Darby

[57] ABSTRACT

The present invention relates to an oral drug delivery system, and in particular to modified amino acid derivatives for use as a delivery system of sensitive agents such as bioactive peptides. The modified amino acid derivatives can form non-covalent mixtures with active biological agents and in an alternate embodiment can releasably carry active agents. These mixtures are suitable for oral administration of biologically active agents to mammals. Methods for the preparation of such amino acids are also disclosed.

24 Claims, 8 Drawing Sheets

U.S. PATENT DOCUMENTS

| | | | |
|---|---|---|---|
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,239,635 | 12/1980 | Rieder. | |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,393,192 | 7/1983 | Curatolo et al. . | |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,690,786 | 9/1987 | Ninomiya et al. . | |
| 4,692,284 | 9/1987 | Braden. | |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,908,233 | 3/1990 | Takizawa et al. | 427/213.35 |
| 4,919,939 | 4/1990 | Baker | 424/493 |
| 4,925,673 | 5/1990 | Stein | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. . | |
| 5,023,374 | 6/1991 | Simon. | |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. . | |
| 5,271,961 | 12/1993 | Mathiowitz et al. | 427/213.31 |
| 5,278,148 | 1/1994 | Baranca et al. | 514/19 |
| 5,310,535 | 5/1994 | Kruper, Jr. et al. | 424/1.53 |
| 5,328,992 | 7/1994 | Peter et al. | 534/116 |
| 5,352,461 | 10/1994 | Feldstein et al | 424/493 |
| 5,384,133 | 1/1995 | Boyes et al. | 424/501 |
| 5,389,377 | 2/1995 | Chagnon et al. . | |
| 5,389,379 | 2/1995 | Dirix et al. | 424/451 |
| 5,401,516 | 3/1995 | Milstein et al. | 424/491 |
| 5,418,010 | 5/1995 | Janda et al. | 427/213.31 |
| 5,443,841 | 8/1995 | Milstein et al. | 424/451 |
| 5,447,728 | 9/1995 | Milstein et al. | 424/490 |
| 5,451,410 | 9/1995 | Milstein et al. | 424/490 |
| 5,536,813 | 7/1996 | Charpenel et al. | 530/324 |
| 5,540,939 | 7/1996 | Milstein et al. | 424/491 |
| 5,578,323 | 11/1996 | Milstein et al. . | |
| 5,601,846 | 2/1997 | Milstein et al. . | |

FOREIGN PATENT DOCUMENTS

| | | | |
|---|---|---|---|
| 2 424 169 | 12/1974 | Germany | A61K 9/00 |
| 2343073 | 3/1975 | Germany. | |
| 3 202 255 | 10/1982 | Germany | C08L 89/00 |
| 3 612 102 | 10/1986 | Germany | C07K 15/00 |
| 71258/2 | 12/1987 | Israel . | |
| 48-24246 | of 1973 | Japan. | |
| 56-68612 | 6/1981 | Japan | A61K 31/19 |
| 6-107682 | 4/1994 | Japan . | |
| 280825 | 12/1964 | Netherlands . | |
| 280826 | 12/1964 | Netherlands . | |
| B-146698 | 11/1982 | Norway | A61K 37/26 |
| 929401 | 6/1963 | United Kingdom . | |
| 1075952 | 8/1967 | United Kingdom . | |
| 1236885 | 6/1971 | United Kingdom . | |
| 1 567 763 | 5/1980 | United Kingdom | A61K 9/22 |
| 2 095 994 | 10/1982 | United Kingdom . | |
| WO 85/00105 | 1/1985 | WIPO | A61K 9/52 |
| WO85/00110 | 1/1985 | WIPO | A61K 47/00 |
| WO 85/02772 | 7/1985 | WIPO | A61K 49/00 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |
| WO 93/25583 | 12/1993 | WIPO | C07K 15/00 |
| WO 94/11015 | 5/1994 | WIPO | A61K 37/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |
| WO 95/28838 | 11/1995 | WIPO | A01N 37/46 |
| WO 95/28920 | 11/1995 | WIPO | A61K 31/19 |
| WO 96/12473 | 5/1996 | WIPO . | |
| WO 96/12474 | 5/1996 | WIPO . | |
| WO 96/12475 | 5/1996 | WIPO . | |

| | | |
|---|---|---|
| WO 96/21464 | 7/1996 | WIPO. |
| WO 96/33699 | 10/1996 | WIPO. |
| WO 96/39835 | 12/1996 | WIPO. |
| WO 96/40070 | 12/1996 | WIPO. |
| WO 96/40076 | 12/1996 | WIPO. |

OTHER PUBLICATIONS

Roulhwai Chen et al., "Evidence for Hemiacetal Formation between N–Acyl–L–phenylalaninals and α–Chymotrypsin by Cross–Saturation Nuclear Magnetic Resonance Spectroscopy", vol. 18, No. 5, pp. 921–925 (1979).

Kenneth R. Davis et al., "Leucinal Inhibits Brain Aminopeptidase Activity and Potentiates Analgesia Induced by Leu–Enkephalin", *Pharmacology Biochemistry & Behavior*, vol. 19, pp. 791–794 (1983).

Charles V. Jackson et al., "Pharmacological Assessment of the Antithrombotic Activity of the Peptide Thrombin Inhibitor, D–Methyl–Phenylalanyl–Prolyl–Arginal (GYK1–14766), in a Canine Model of Coronary Artery Thrombosis", *The Journal of Pharmacology And Experimental Therapeutics*, vol. 261, No. 1, pp. 546–552 (1992).

Airaudo, C.B. et al. (1987) *Journal of Food Science*, vol. 52(6), pp. 1750–1752.

Andini, S. et al. (1975) *Origins of Life*, vol. 6, pp. 147–153.

Brooke, S. 1 et al. (1977) *BioSystems*, vol. 9, pp. 1–22.

Chen et al. (1975) "Evidence for Hemiacetal Formation", *Biochemistry*, vol. 18, No. 5, pp. 921–925.

Davis et al. (1983) "Leucinal Inhibits . . . ", *Pharmacology Biochemistry Behavior*, vol. 19, pp. 791–794.

Dose, K. (1974) *Origins of Life*, vol. 5, pp. 239–252.

Fasman et al. (1964) *Biochemistry*, vol. 3, No. 11, pp. 1665–1674.

Fox, S.W. et al. (1976) *BioSystems*, vol. 8, pp. 40–44.

Fox, S.W. et al., *Molecular Evolution and the Origin of Life*, Maxel Decker, New York (1977).

Fox, S.W. et al. (1968) *Biochim. Biophys. Acta*, vol. 160, pp. 246–249.

Fox, S.W. (1976) *Origins of Life*, vol. 7, pp. 49–68.

Fox, S.W. (1980) *Naturwissenschaften*, vol. 67, pp. 378–383.

Fox, S.W. et al. (1960) *Archives of Biochemistry and Biophysics*, vol. 86, pp. 281–285.

Fox, S.W. et al. (1974) *Origins of Life*, vol. 5, pp. 227–237.

Fox, S.W. (1984) *Origins of Life*, vol. 14, pp. 485–488.

Gol'dovskii, A.M. (1978) *Zhurnal Evolyusionnoi Biokhimii i Fiziologii*, vol. 14(6), pp. 517–519.

Gurrieri, S. et al. (1973) *Thermochimica Acta*, vol. 7, pp. 231–239.

Harada, K. et al. (1979) *BioSystems*, vol. 11, pp. 47–53.

Harada et al. (1960) *Archives of Biochemistry and Biophysics*, vol. 86, pp. 274–280.

Hare (1970) *Etude Cenetique De La Polycondensation Thermique D'χ–Amino Acides*, vol. 45, pp. 330–339.

Heinrich, M.R. et al. (1969) *Archives of Biochemistry and Biophysics*, vol. 130, pp. 441–448.

Heinz, B. et al. (1981) *BioSystems*, vol. 14, pp. 33–40.

Hennon, G. et al. (1975) *Biochimie*, vol. 57, pp. 1395–1396.

Hsu, L.L. et al. (1976) *BioSystems*, vol. 8, pp. 89–101.

Hsu, L.L. et al. (1971) *Currnts in Modern Biology*, vol. 4, pp. 12–25.

Ishima, Y. et al. (1981), *BioSystems*, vol. 14, pp. 243–251.

Jackson et al. (1991) "Pharmacological . . . ", *J. Pharm. & Exp. Thera.*, vol. 261, No. 1, pp. 546–552.

Jungck, J.R. et al. (1973) *Naturwissenschaften*, vol. 60, pp. 425–427.

Kokufuta, E. et al. (1984) *BioSystems*, vol. 16, pp. 175–181.

Krampitz, G. et al. (1967) *Naturwissenschaften*, pp. 516–517.

Krampitz, G. et al. (1968) *Naturwissenschaften*, pp. 345 and 346.

Krampitz, G. et al. (1966) *Naturwissenschaften*, pp. 7 and 8.

Lacey, Jr., J.C. et al. (1979) *BioSystems*, vol. 11, pp. 9–17.

Lacey, Jr., J.C. et al. (1979) *BioSystems*, vol. 11, pp. 1–7.

Martinez Luque–Romero, M. et al. (1986) *BioSystems*, vol. 19, pp. 267–272.

Masinovsky, Z. et al. (1989) *BioSystems*, vol. 22, pp. 305–310.

Matsuno, K. (1982) *BioSystems*, vol. 15, pp. 1–11.

Matsuno, K. (1984) *BioSystems*, vol. 17, pp. 11–14.

Matsuno, K. (1981) *BioSystems*, vol. 14, pp. 163–170.

McAlhaney, W.W. et al. (1976) *BioSystems*, vol. 8, pp. 45–50.

Melius, P. et al. (1987) *BioSystems*, vol. 20, pp. 213–217.

Melius, P. et al. (1975) *Bioorganic Chemistry*, vol. 4, pp. 385–391.

Melius, P. (1979) *BioSystems*, vol. 11, pp. 125–132.

Miquel, J. et al. (1971) *Currents in Modern Biology*, vol. 3, pp. 299–306.

Nakashima, T. et al. (1980) *J. Mol. Evol.*, vol. 15, pp. 161–168.

Nakashima, T. et al. (1981) *BioSystems*, vol. 14, pp. 151–161.

Novak, V.J.A. (1984) *Origins of Life*, vol. 14, pp. 513–522.

Olafsson, P.G. et al. (1971) *Polymer Letters*, vol. 9, pp. 521–528.

Phillips, R.D. et al. (1974) *Int. J. Peptide Protein Res.*, vol. 6, pp. 309–319.

Przybylski, A.T. et al. (1982) *Die Naturwissenschaften*, vol. 69, pp. 561–563.

Przybylski, A.T. et al. (1984) *Applied Biochemistry and Biotechnology*, vol. 10, pp. 301–307.

Przybylski, A.T. (1985) *BioSystems*, vol. 17, pp. 281–288.

Rohlfing, D.L. (1975) *Origins of Life*, vol. 6, pp. 203–209.

Rohlfing, D.L. (1970) *Science*, vol. 169, pp. 998–1000.

Rohlfing, D.L. et al. *Catalytic Activities of Thermal Polyanhydro–α–Amino Acids*, pp. 373–418.

Rohlfing, D.L. et al. (1976) *BioSystems*, vol. 8, pp. 139–145.

Ryan, J.W. et al. (1973) *BioSystems*, vol. 5, pp. 115–118.

Saunders, M.A. et al. (1974) *BioSystems*, vol. 6, pp. 81–92.

Snyder, W.D. et al. (1975) *BioSystems*, vol. 7, pp. 222–229.

Sokol, P.E. (1974) *Journal of the American Oil Chemists' Society*, vol. 52, pp. 101–102.

Tschager et al. (1989) *Milchwirtschaftliche Berichte*, vol. 95, pp. 79–83.

Vaughan, G. et al. (1987) *BioSystems*, vol. 20, pp. 219–223.

Vol'kenshtein, M.V. (1989) *Molekulyarnaya Biologiya*, vol. 23(1), pp. 23–37.

Waehneldt, T.V. et al. (1968) *Biochim. Biophys. Acta*, vol. 160, pp. 239–245.

Williams et al. (1991) *J. Biol. Chem.*, vol. 266, No. 8, pp. 5182–5190.

Yuki, A. et al. (1969) *Biochemical and Biophysical Research Communications*, vol. 36(4), pp. 657–663.

Zulaski et al. (1983) "New Carboxyalkyl Inhibitors of Brain Enkenphalinase", *J. Med. Chem.*, 26, pp. 60–65.

(1985) *Chemical Abstracts*, vol. No. 105(1), Abstract No. 12027p.

(1985) *Chemical Abstracts*, vol. No. 102(6), Abstract No. 50870d.

Bergeron, Raymond J., et al. (1994) "Macromolecular Self–Assembly of Diketopiperazine Tetrapeptides", *Journal of the American Chemical Society*, vol. 116, pp. 8479–8484.

Bergeron, Raymond J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.

Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharmacological Research Communications* 17(8):685–697.

Dal Pozzo, A., et al. (1989), *Thrombosis Research* 56:119–124.

Airaudo, C.B., et al. (1987), *Journal of Food Science* 52(6):1750–1752.

Gelb, R., et al (1983), *Lite Sciences* 33(1):83–85.

Watterberg et al. (1988), *Pediatric Research*, vol. 23, No. 4, part 2, p. 570A, col. 1, abstract No. 2209.

Bernstein (1985), *Chest* 87(1):68S–73S.

Damage et al. (1988), *Diabetes* 37:246–251.

184358, *chemical Abstracts*:83 (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utal*, Feb. 22–25, 1993, Salt Lake City, UT, pp. 179–180.

Haas, S. et al., "Assessment Of Stability Of Proteinoid Microspheres", *Proceed. Intern. Symp. Control. Rel. Bioact. Mater.*, 20 (1993), Controlled Release Society, Inc.

X. Ma, et al., *Proceed. Intern. Symp. Control. Rel. Bioact. Mater.*, 20 (1993), Controlled Release Society, Inc.

Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at "IBC Rational Drug Design Conference", San Diego, Calif.—Dec. 1994.

Bergeron, Raymond J. et al., *J. Am. Chem. Soc.* 1994, 116,8479–8484.

Leone–Bay et al., Presented at "Winter Conference on Medicinal and Bioorganic Chemistry" Steamboat Springs, Colorado—Feb. 1995.

Santiago et al., *Pharm. Res.* 11: 1994, p.S–298.

Leone–Bay et al., *Pharm. Res.* 11: 1994, p.S–121.

Sarrubbi et al., *Pharm. Res.* 11: 1994, p.S–299.

Leipold et al., *Pharm. Res.* 11: 1994, p.S–298.

X. Ma et al., PDD 7303 *Pharmaceutical Research* 9(10):S–244, 1992 (Oct. Supplement).

Milstein et al., *Symposia Abstracts*. AAPS Annual Meeting, San Antonia, TX, Nov. 15–19, 1993.

Santiage et al. "Initial Studies In The Assessment of Proteinoid Microsphere Activity" *Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., pp. 116–117.

Santiago et al. "Proteinoid Microspheres For The Oral Delivery of Heparin" *Proceed. Intern. Symp. Control. Rel. Bioact. Mater.*, 19 (1992), Controlled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.*, 19 (1992), Controlled Release Society, Inc. pp. 516–517.

Doris K. Chiappetta, *Eastern Analytical Symposium*, Nov. 17, 1992.

Elizabeth A. Harris, M.S., *Eastern Analytical Symposium*, Nov. 17, 1992.

*AAPS 6TH Ann. Meeting and Expo.*, "Proteinoids—A Novel Drug Delivery System" Nov. 19, 1992, p.33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

*Journal of Medicinal Chemistry*, vol. 38, No. 21, pp. 4257–4262, (1995), "Microsphere Formation in a Series of Derivatized α–Amino Acids: Properties, Molecular Modeling, and Oral Delivery of Salmon Calcitonin".

*Journal of Medicinal Chemistry*, vol. 38, No. 21, pp.4263–4269, (1995), "N–Acylated α–Amino Acids as Novel Oral Delivery Agents for Proteins".

Robert O. Dillman, M.D., Annals of Internal Medicine 1989:111 pp. 592–600, "Monoclonal Antibodies for Treating Cancer".

Brendan D. Curti, Critical Reviews in Oncology/Hematology, 1993: 14 pp. 29–29 "Physical barriers to drug delivery in tumors".

V. Hird et al, Genes and Cancer, edited by Desmond Carney & Karol Sikora, pp.183–189, "Immunotherapy with Monoclonal Antibodies", 1990.

Michael E. Osband et al. Immunology Today, vol. 11, No.6 1990, pp. 93–95, "Problems in the investigational study and clincal use of cancer immunotherapy".

Tibtech Feb. 1993 vol.11, pp. 42–44 "Therapeutic antibodies—the coming of age".

Thomas A. Waldmann, Articles Jun. 21, 1991, pp. 1657–1662, "Monoclonal Antibodies in Diagnosis and Therapy".

- ■ — sCT 1.5 μg/kg
- ● — Phenylsulfonyl aminophenyl butyrate 400 mg/kg + sCT 1.5 μg/kg
- ▲ — Phenylsulfonyl aminophenyl butyrate 200 mg/kg / Phe-al 200 mg/kg + sCT 1.5 μg/kg

ORAL DRUG DELIVERY COMPOSITIONS AND METHODS

FIELD OF THE INVENTION

The present invention relates to compositions suitable for oral drug delivery, and in particular to compositions in which modified amino acid derivatives are used as carriers for sensitive agents such as bioactive peptides and the like. The modified amino acid derivatives can form non-covalent mixtures with biologically-active agents and are suitable for oral administration to mammals. Methods for the preparation for the administration of such compositions are also disclosed.

BACKGROUND OF THE INVENTION

Conventional means for delivering biologically-active agents, including, but not limited to, pharmaceutical and therapeutic agents to mammals are often severely limited by chemical barriers and physical barriers, imposed by the body. Oral delivery of many biologically-active agents would be the route of choice if not for the presence of chemical and physico-chemical barriers such as the extreme and varying pH in the gut, exposure to powerful digestive enzymes, and the impermeability of gastrointestinal membranes to the active agent. Among the numerous agents which are not suitable for oral administration are biologically-active peptides such as calcitonin and insulin. Other compounds which are affected by the physico-chemical barriers of the gut are polysaccharides and particularly mucopolysaccharides, including, but not limited to, heparin; heparinoids; antibiotics; and other organic substances. These agents are rapidly destroyed in the gut by acid hydrolysis, enzymes, or the like.

Prior methods for orally administering vulnerable pharmacological agents have relied on the co-administration of adjuvants (e.g., resorcinols and non-ionic surfactants such as polyoxyethylene oleyl ether and n-hexadecyl polyethylene ether) to increase artificially the permeability of the intestinal walls; and on the co-administration of enzymatic inhibitors (e.g., pancreatic trypsin inhibitor, diisopropylfluorophosphate (DFF) and TRASYLOL) to avoid enzymatic degradation. Liposomes have also been described as drug delivery systems for insulin and heparin. See, for instance, U.S. Pat. No. 4,239,754; Patel et al. (1976) FEBS Letters Vol. 62, page 60; and Hashimoto et al. (1979) Endocrinol. Japan, Vol. 26, page 337. However, in the broad spectrum use of the aforementioned drug delivery systems is precluded for reasons including: (1) the need to use toxic amounts of adjuvants or inhibitors; (2) the lack of suitable low MW cargoes; (3) the poor stability and inadequate shelf life of the systems; (4) the difficulties in manufacturing them; (5) the failure of the systems to protect the active ingredient; and (6) the failure of the systems to promote absorption of the active agent.

More recently, artificial amino acid compositions or proteinoid forming microspheres have been described for encapsulating pharmaceuticals. For example, U.S. Pat. No. 4,925,673 describes such microsphere constructs as well as methods for their preparation and use. These proteinoid microspheres are useful for encapsulating a number of active agents. However, the preparation of these microspheres yields a complex mixture of high molecular weight (MW) (>1000 daltons) and low MW (≦1000 daltons) peptide-like polymers which are difficult to separate. Furthermore, relatively small amounts of the low MW microsphere-forming fraction are produced. Thus, there is a need in the art for a simple and inexpensive delivery system which is easily prepared and which can deliver a broad range of biologically-active agents.

SUMMARY OF THE INVENTION

The present invention relates to modified amino acid derivatives for use in oral delivery compositions for biologically-active agents. These compositions can incorporate modified amino acid derivative as carriers. These pharmacological compositions comprise (A) at least one biologically-active agent; and
(B) at least one carrier comprising
  (a) (i) at least one acylated aldehyde of an amino acid,
    (ii) at least one acylated ketone of an amino acid,
    (iii) at least one acylated aldehyde of a peptide,
    (iv) at least one acylated ketone of a peptide, or
    (v) any combination of (a)(i), (a)(ii), (a)(iii) and (a)(iv);
  (b) (i) carboxymethyl-phenylalanine-leucine,
    (ii) 2-carboxy-3-phenylpropionyl-leucine,
    (iii) 2-benzylsuccinic acid, or
    (iv) or any combination of (b)(i), (b)(ii) and (b)(iii); or
  (c) a combination of (a) and (b).

In an alternative embodiment, a method for orally administering the biologically-active agents with the compositions above is provided. Also contemplated is a method for preparing the pharmacological compositions which comprises mixing at least one biologically active agent, with at least one carrier as described above, and optionally, a dosage vehicle.

The modified amino acid derivatives are non-toxic and can be orally administered to mammals as part of a drug delivery system by blending or mixing the modified amino acid derivatives with a biologically active agent prior to administration to a subject. Also contemplated by the present invention are dosage unit forms that include these compositions.

DESCRIPTION OF THE DRAWINGS

FIG. 1 is a graphic illustration of the results of oral gavage testing of the present invention in rats.

FIG. 1 is a graphic illustration of the results of oral gavage testing in rats using salmon calcitonin with acetyl phenylalanine aldehyde, carbomethoxyPhe-Leu-OH, and acetyl-Phe-Leu-Leu-Arg aldehyde carriers.

FIG. 2 is a graphic illustration of the results of oral gavage testing in rats using salmon calcitonin with acetylleucine aldehyde and acetylphenylalanine aldehyde carriers.

FIG. 3 is a graphic illustration of the results of oral gavage testing in rats using salmon calcitonin with acetylphenylalanine aldehyde and carbomethoxyPhe-Leu-OH carriers.

FIG. 4 is a graphic illustration of the results of oral gavage testing in rats using salmon calcitonin with acetylphenylalanine aldehyde, acetylLeu-Leu-Arg aldehyde and carbomethoxyPhe-Leu-OH carriers.

FIG. 5 is a graphic illustration of the results of intraduodenal injection testing in rats using salmon calcitonin with acetylphenylalanine aldehyde and 4-(phenylsulfonamido)-4-phenylbutyric acid carriers.

FIG. 6 is a graphic illustration of the results of oral gavage testing in rats using salmon calcitonin with acetylphenylalanine aldehyde, N-acetyllysinone, and acetyl-Leu aldehyde carriers.

FIG. 7 is a graphic illustration of the results of intraduodenal injection testing in rats using salmon calcitonin with acetylphenylalanine aldehyde carrier in aqueous ethanol, dimethyl sulfoxide (DMSO), and olive oil dosing vehicles, and in a DMSO dosing vehicle alone.

FIG. 8 is a graphic illustration of the results of oral gavage testing in rats using salmon calcitonin with cyclohexanoylphenylalanine aldehyde carrier.

DETAILED DESCRIPTION OF THE INVENTION

Figure 1:
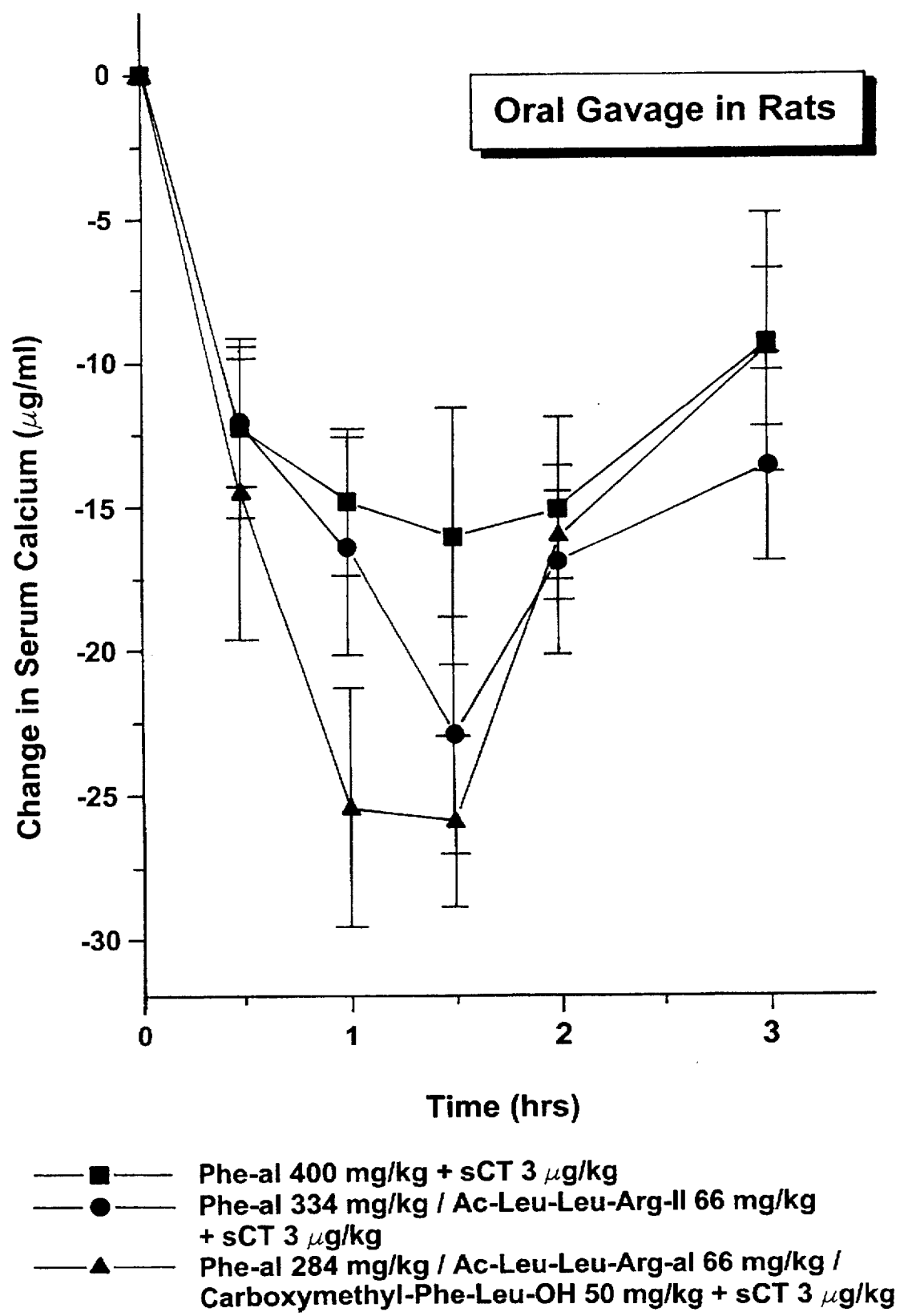
FIGS. 1–8 are graphic illustrations of the results of oral gavage testing in rats.

The present invention arose from the discovery that amino acid derivatives, in modified form, may be used to deliver orally sensitive biologically-active agents, including, but not limited to, calcitonin, hormones such as insulin, and polysaccharides such as heparin, which would not be considered orally administrable for various reasons. Insulin, for example is sensitive to the denaturing conditions of the gastro-intestinal (GI) tract. Also, heparin, by virtue of its charge and hydrophilic nature, is not readily absorbed from the gut. In contrast to the modified amino acid derivatives of the present invention, unmodified free amino acids provide inadequate protection against degradation in the GI tract for labile bioactive agents.

Other advantages provided by the present invention include the use of readily available and inexpensive starting materials in a cost-effective method for preparing and isolating modified amino acid derivatives which is simple to perform and is amenable to industrial scale-up production.

Biologically-active agents suitable for use with carriers disclosed herein include, but are not limited to, peptides, and particularly small peptide hormones, which by themselves pass slowly or not at all through the gastro-intestinal mucosa and/or are susceptible to chemical cleavage by acids and enzymes in the gastrointestinal tract; polysaccharides and particularly mixtures of mucopolysaccharides, carbohydrates; lipids; or any combination thereof. Examples include, but are not limited to, human growth hormone; bovine growth hormone; growth hormone releasing hormone; interferons; interleukin-I; insulin; heparin, and particularly low molecular weight heparin; calcitonin; erythropoietin; atrial naturetic factor; antigens; monoclonal antibodies; somatostatin; adrenocorticotropin; gonadotropin releasing hormone; oxytocin; vasopressin; vancomycin; desferrioxamine (DFO); or any combination thereof.

The term amino acid as used herein includes any carboxylic acid having at least one free amine group including naturally occurring and synthetic amino acids. The preferred amino acids are α-amino acids, and preferably are naturally occurring α-amino acids.

Poly amino acids as used herein can refer to peptides or two or more amino acids linked by a bond formed by other groups which can be linked, e.g., an ester, anhydride or an anhydride linkage.

The term peptide is meant to include two or more amino acids joined by a peptide bond. Peptides include those materials defined in *Chambers Biological Dictionary*, editor Peter M. B. Walker, Cambridge, England: Chambers Cambridge, 1989, page 215, which states that a "peptides can vary in length from dipeptides with 2 to poly peptides with several hundred amino acids." The peptides most useful in the practice of the present invention include di-peptides, tri-peptides, tetra-peptides, and penta-peptides. The preferred peptides are di-peptides, tri-peptides. Peptides can be homo- or hetero-peptides and can include natural amino acids, synthetic amino acids, or any combination thereof.

The preferred naturally occurring amino acids for use in the present invention as amino acids or components of a peptide are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, phenylglycine, or O-phosphoserine.

The preferred non-naturally occurring amino acids for use in the present invention are β-alanine, α-amino butyric acid, γ-amino butyric acid, α-amino isobutyric acid, ε-amino caproic acid, 7-amino heptanoic acid, β-aspartic acid, γ-glutamic acid, cysteine (ACM), ε-lysine, ε-lysine (A-Fmoc), methionine sulfone, norleucine, norvaline, ornithine, d-ornithine, p-nitro-phenylalanine, hydroxy proline, and thioproline.

The amino acid or peptide derivatives of the present invention can be readily prepared by reduction of amino acid esters or peptide esters with an appropriate reducing agent. For example, amino acid or peptide aldehydes can be prepared as described in an article by R. Chen et al., *Biochemistry*, 1979, 18, 921-926. Amino acid or peptide ketones can be prepared by the procedure described in *Organic Syntheses*, Vol. IV, Wiley, (1963), pages 5. Amino acids, peptides, amino acid esters, peptide esters, and other necessary reagents to prepare these derivatives are readily available from a number of commercial sources such as Aldrich Chemical Co. (Milwaukee, Wis., USA); Sigma Chemical Co. (St. Louis, Mo, USA); and Fluka Chemical Corp. (Ronkonkoma, N.Y., USA).

According to the invention, the modified amino acid or peptide derivatives are amino acids or peptides which have had at least one acyl-terminus converted to an aldehyde or a ketone and are acylated at at least one free amine group, with an acylating agent which reacts with at least one of the free amine groups present. Suitable, but non-limiting, examples of agents useful for modifying amino acids in practicing the present invention include acid chloride acylating agents of the formula R—CO—X wherein R is alkyl and preferably lower alkyl having from 1 to about 20 carbon atoms, cycloalkyl and preferably cycloalkyl having from 1 to about 20 carbon atoms, or aromatic and preferably aromatic having from 6 to about 20 carbon atoms. Preferably, R is methyl, ethyl, cyclohexyl, cyclopentyl, phenyl or benzyl. Preferably, R—CO is cyclohexyl or acetyl. X is a leaving group. In *Advanced Organic Chemistry*, 2d edition, Jerry March, New York: McGraw-Hill Book (1977) states, "In a reaction in which the substrate molecule becomes cleaved, part of it (the part not containing the carbon) is usually called the leaving group." Typical leaving groups include, but are not limited to, halogens such as chlorine, bromine and iodine.

These agents include, but are not limited to, acetyl chloride, propyl chloride, cyclohexanoyl chloride, benzoyl chloride, hippuryl chloride and the like; as well as anhydrides, including, but not limited to, acetic anhydride, propyl anhydride, cyclohexanoic anhydride, benzoic anhydride, hippuric anhydride and the like.

In a peptide one or more of the amino acids may be derivatized (an aldehyde or a ketone) and/or modified (acylated).

Also suitable as a carrier alone or in combination with the modified amino acid or peptide derivatives are the carbomethoxy modified amino acids carboxy-methyl-phenylalanine-leucine, 2-carboxy-3-phenylpropionyl-leucine and 2-benzylsuccinic acid.

For example, the modified amino acid derivatives of the present invention may be prepared by reacting a single amino acid or peptide derivative or mixtures of two or more amino acid or peptide derivatives, with an acylating agent or an amine modifying agent which reacts with free amino moieties present in the derivatives to form amides. The amino acid or peptide can be modified and subsequently derivatized, derivatized and subsequently modified, or simultaneously modified and derivatized. Protecting groups may be used to avoid unwanted side reactions as would be known to those skilled in the art.

Suitable modified amino acid derivatives include, but are not limited to, N-cyclohexanoyl-Phe aldehyde, N-acetyl-Phe-aldehyde, N-acetyl-Tyr ketone, N-acetyl-Lys ketone and N-acetyl-Leu ketone. Special mention is made of the modified amino acid derivative N-cyclohexanoyl phenylalanine aldehyde. Most preferred are arginine, leucine, lysine, phenylalanine, tyrosine, valine, and phenylglycine. Most preferred are arginine, leucine, lysine, phenylalanine, tyrosine, valine, and phenylglycine.

Special mention is made of compositions in which the biologically-active agent includes, calcitonin and the carrier includes acetyl phenylalanine aldehyde, carbomethoxy phenylalanyl-leucine and acetyl-Phe-Leu-Leu aldehyde.

Special mention is also made of a composition which includes 1.5 μg/ml of the biologically-active agent calcitonin and the carrier includes 132 mg/ml of acetyl phenylalanine, 33 mg/ml of carbomethoxy phenylalanylleucine, and 25 mg/ml of Bacetyl-Phe-Leu-Leu-Arg aldehyde SEQ ID NO: 1.

Typically, the pharmacological compositions of the present invention are prepared by mixing an aqueous solution of the carrier with an aqueous solution of the active ingredient. Just prior to administration, the carrier and biologically active ingredient can be admixed during the manufacturing process. The solutions may optionally contain additives such as phosphate buffer salts, citric acid, acetic acid, gelatin and gum acacia.

A solution of the modified amino acid derivatives can be prepared by mixing the amino acid derivatives in aqueous solution in an amount ranging between about 1 mg and about 1.5 g, preferably ranging between about 1 mg and about 800 mg per mL of solution. The final solution contains between about 1 mg and about 2000 mg of modified amino acid derivatives per mL of solution and, preferably, between about 1 mg and about 800 mg per mL. The concentration of active agent in the final solution varies and is dependent on the required dosage for treatment. The exact concentration can be determined by reverse phase HPLC analysis.

In practicing the invention, stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, and polylysine. The preferred stabilizing additives are gum acacia, gelatin and methyl cellulose.

The amount of active agent in the composition typically is a pharmacologically effective amount. However, the amount can be less than a pharmacologically effective amount when the composition is used in a dosage unit form, such as a capsule, a tablet or a liquid, because the dosage unit form contains a multiplicity of carrier/biologically-active agent compositions, the total of which will include the pharmacologically active amount of biologically-active agent.

The total amount of biologically-active agent to be used can be determined by those skilled in the art. However, it has surprisingly been found that with certain biologically-active agents, such as calcitonin, the use of the presently disclosed carriers provides extremely efficient delivery. Therefore, lower amounts of biologically-active agent than those used in prior dosage unit forms or delivery systems can be administered to the subject, while still achieving the same blood levels and therapeutic effects.

The amount of carrier in the present composition is a delivery effective amount and can be determined for any particular carrier or biologically-active agent by methods known to those skilled in the art.

Dosage unit forms can also include any of excipients; diluents; disintegrants; lubricants; plasticizers; colorants; dosage vehicles, including, but not limited to water, 1,2-propane diol, ethanol, olive oil or any combination thereof.

Administration of the present compositions or dosage unit forms is oral.

EXAMPLES

The invention will now be illustrated in the following non-limiting examples which are illustrative of the invention but are not intended to limit the scope of the invention.

Example 1

Preparation of N-Cyclohexanoylphenylalanine Aldehyde:

Phenylaline methyl ester (1 g., 0.0046 moles) was dissolved in pyridine 5 mL. Cyclohexanoyl chloride (0.62 mL) was added and the mixture was stirred for 2 hours. The reaction mixture was poured onto hydrochloric acid (1N) and crushed ice. The aqueous mixture was extracted twice with toluene. The combined toluene extracts were concentrated in vacuo to give 1.1 g of crude N-cyclohexanoylphenylalanine methyl ester.

N-Cyclohexanoylphenylalanine methyl ester (0.5 g) was dissolved in ethylene glycol dimethyl ether (20 mL). The solution was cooled to −70° C. and diisobutylaluminum hydride (2.04 mL of a 1.5M solution in toluene) was added. The resulting reaction mixture was stirred at −70° C. for 2 hours. The reaction was quenched by dropwise addition of 2N hydrochloric acid. The mixture was extracted with cold ethyl acetate. The ethyl acetate solution was washed with brine and dried over sodium sulfate. Concentration in vacuo furnished a white solid which was purified by silica gel chromatography. Mass Spec.: M+1 m/e 261.

Example 2

Preparation of N-Acetylphenylalanine Aldehyde:

N-Acetylphenylalanine methyl ester (4.2 g, 19 mmol) was dissolved in ethylene glycol dimethyl ether. The solution was cooled to −70° C. and diisobutylaluminum hydride (25.3 mL of a 1.5M solution in toluene, 39 mmol) was added. The resulting reaction mixture was stirred at −70° C. for 2 hours. The reaction was quenched by addition of 2N hydrochloric acid. The mixture was extracted 4 times with cold ethyl acetate and 4 times with toluene. The extracts were combined, washed with brine and dried over magnesium sulfate. Concentration in vacuo followed by silica gel chromatography furnished 2.7 g of a white solid. The NMR was identical to that reported in the literature, *Biochemistry*, 1979, 18, 921–926.

Example 3
Preparation of N-Acetyltyrosinone:

A mixture of tyrosine (28.9 g, 16 mmol), acetic anhydride (97.9 g, 96 mmol) and pyridine (35g, 16 mmol) were heated to 100° C. for 1 hour. The reaction mixture was concentrated in vacuo to furnish a yellow oil. The oil was distilled at reduced pressure to furnish 29.9 g or an oil. $^1$H NMR (DMSO-d6):

Example 4
N-Acetyllysinone:

Following the procedure of Example 3 lysine was converted to N-acetyllysinone.

Example 5
N-Acetylleucinone:

Following the procedure of Example 3 leucine was converted to N-acetylleucinone.

Example 6
Preparation of Dosing Solutions:

In a test tube 568 mg of acetyl phenylalanine aldehyde, 132 mg of carbomethoxy phenylalanylleucine and 100 mg acetyl-Phe-Leu-Leu-Arg aldehyde SEQ ID NO:1 were added to 2.9 ml of 15% ethanol. The solution was stirred and NaOH (1.0N) was added to raise the pH to 7.2. Water was added to bring the total volume to 4.0 mL. The sample had a carrier concentration of 200 mg/mL. Calcitonin (6 µg) was added to the solution. The total calcitonin concentration was 1.5 µg/mL.

Following a similar procedure a second solution having 668 mg of acetyl phenylalanine aldehyde and 132 mg of carbomethoxy phenalanylleucine as the carrier composition and a third solution having as the carrier acetyl phenylalanine aldehyde. Each solution had a calcitonin concentration of 1.5 µ/mL.

Example 7
In Vivo Experiments in Rats

For each sample six fasted rats were anesthetized. The rats were administered, by oral gavage, one of the calcitonin/carrier dosages prepared in Example 6. The calcitonin concentration in each sample was 1.5 µg/ml. Each rat was administered a dosage of two (2) mL/kg each. Blood samples were collected serially from the tail artery. Serum calcium was determined by testing with a Demand™ Calcium Kit (available from Sigma Chemical Company, St. Louis, Mo., USA). The results of the test are illustrated in FIG. 1.

Example 8

Figure 2:
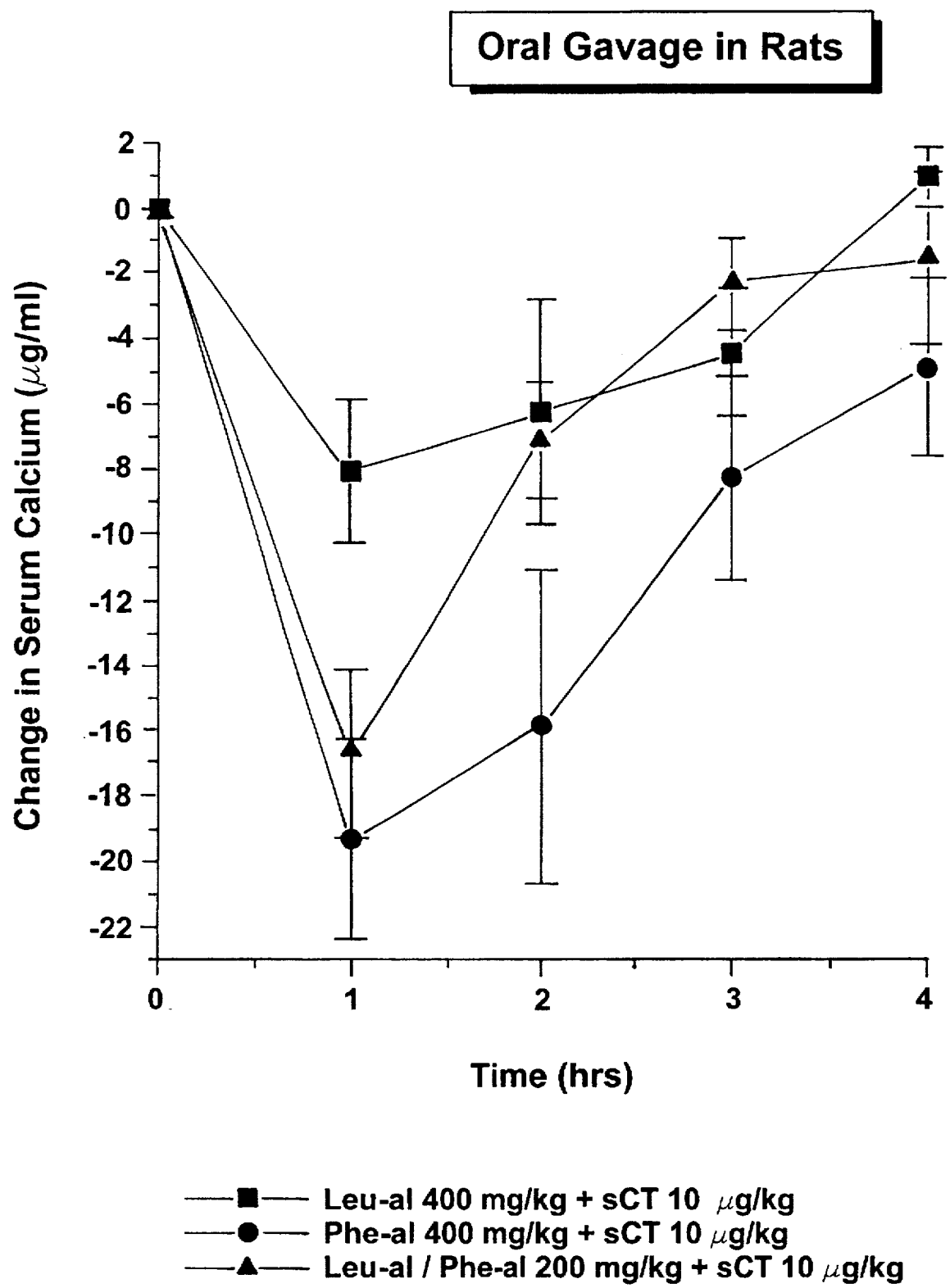

Three samples having 400 mg/kg of acetyl-Leu aldehyde and 10 µg/kg of calcitonin, 400 mg/kg of acetyl-Phe aldehyde and 10 µg/kg of calcitonin, 200 mg/kg of acetyl-Leu aldehyde, 200 mg/kg of acetyl-Phe aldehyde and 10 µg/kg of calcitonin, respectively were prepared. The samples were given to fasted rats as described in Example 7. The results of the test are illustrated graphically in FIG. 2.

Example 9

Figure 3:
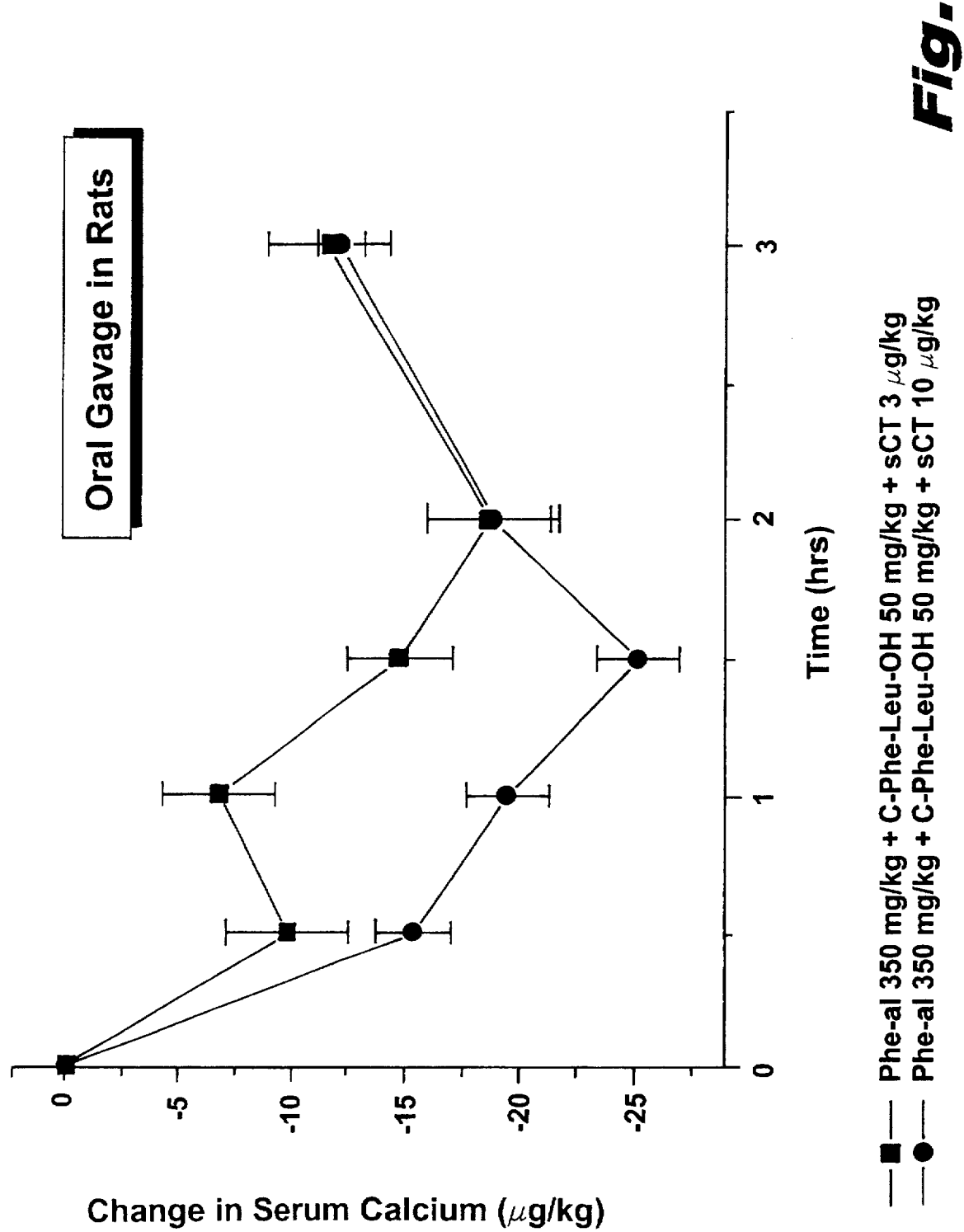

Two samples having 350 mg/kg of acetyl-Phe aldehyde, 50 mg/kg of carbomethoxy-Phe-Leu-OH and 3 µg/kg of calcitonin, 400 mg/kg of acetyl-Phe aldehyde, 50 mg/kg of carbomethoxy-Phe-Leu-OH and 10 µg/kg of calcitonin, respectively were prepared. The samples were given to fasted rats as described in Example 7. The results of the test are illustrated in FIG. 3.

Example 10

Figure 4:
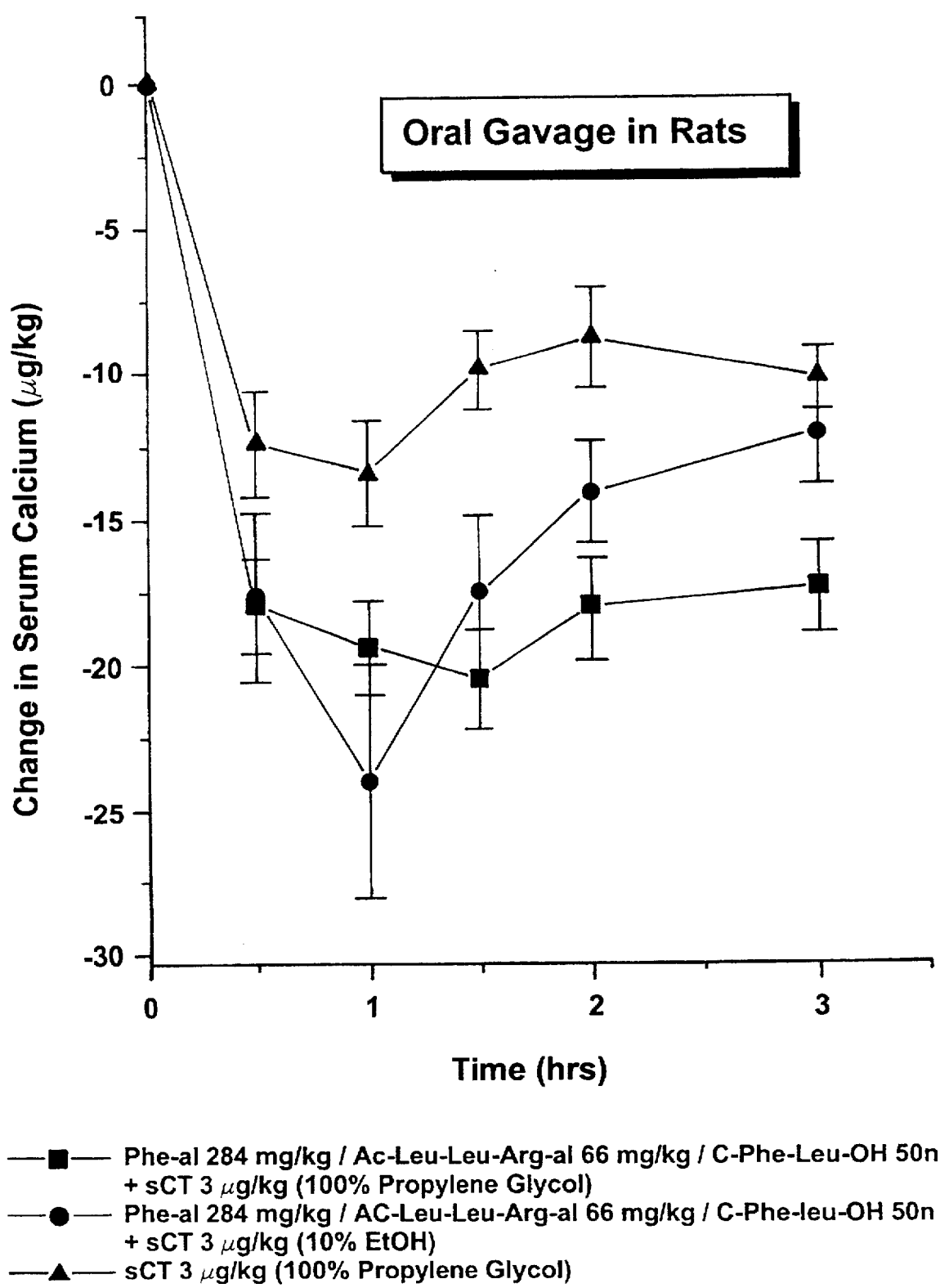

Three samples having 284 mg/kg of acetyl-Phe aldehyde and 66 mg/kg acetyl-Leu-Leu-Arg aldehyde, 50 mg/kg of carbomethoxy-Phe-Leu-OH and 3 µg/kg of calcitonin in propylene glycol, 284 mg/kg of acetyl-Phe aldehyde and 66 mg/kg acetyl-Leu-Leu-Arg aldehyde, 50 mg/kg of carbomethoxy-Phe-Leu-OH and 3 µg/kg of calcitonin and 3 µg/kg of calcitonin, in aqueous ethanol, respectively were prepared. The samples were given to fasted rats as described in Example 7. The results of the test are illustrated in FIG. 4.

Example 11

Figure 5:
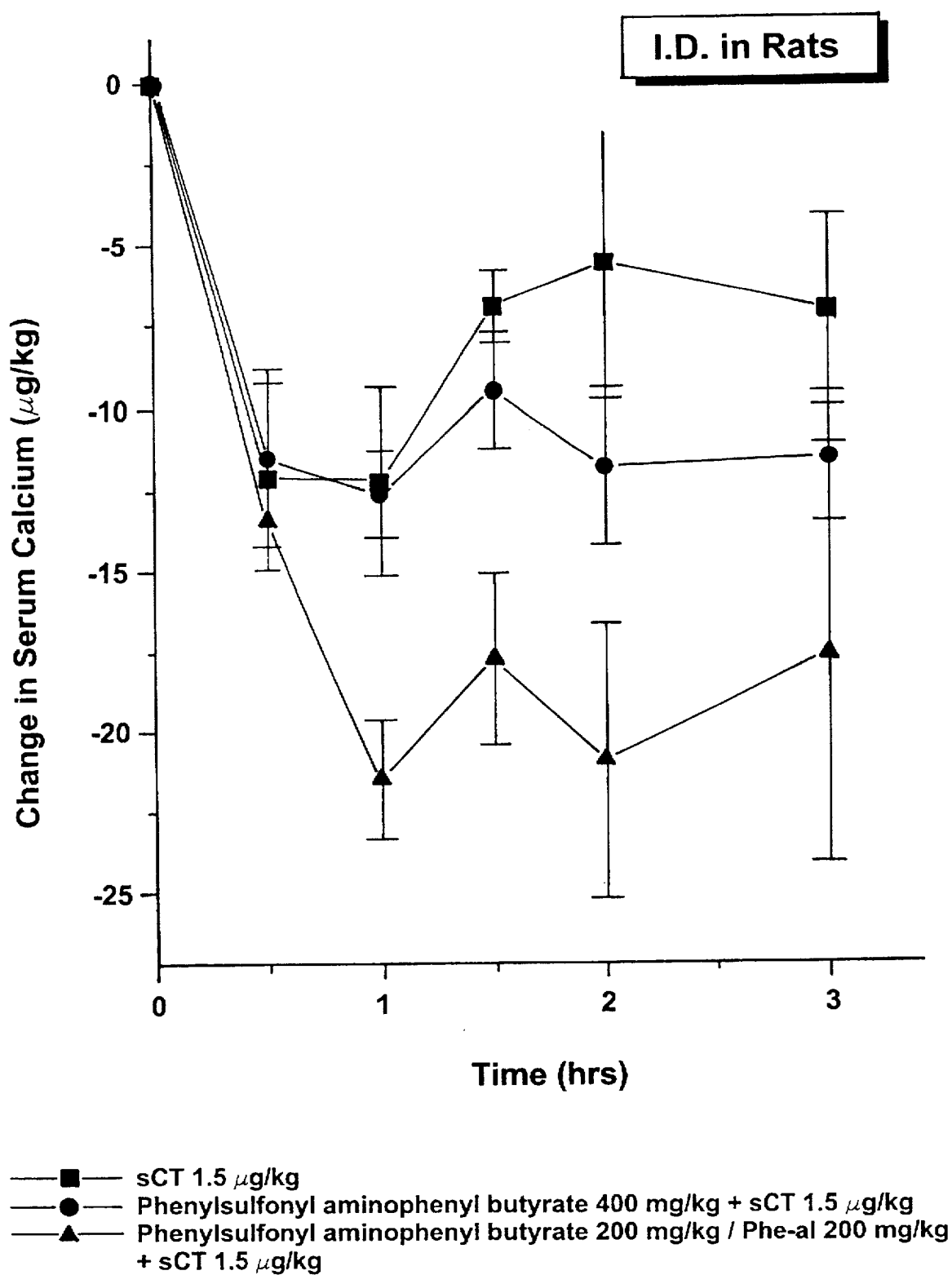

Three samples having 400 mg/kg of phenylsulfonyl aminophenyl-butyric acid and 1.5 µg/kg of calcitonin in propylene glycol, 200 mg/kg of phenylsulfonyl aminophenyl-butyric acid, 200 mg/kg of acetyl-Phe aldehyde and 1.5 µg/kg of calcitonin in aqueous ethanol, respectively were prepared. The samples were given to fasted rats as described in Example 7. The results of the test are illustrated in FIG. 5.

Example 12

Figure 6:
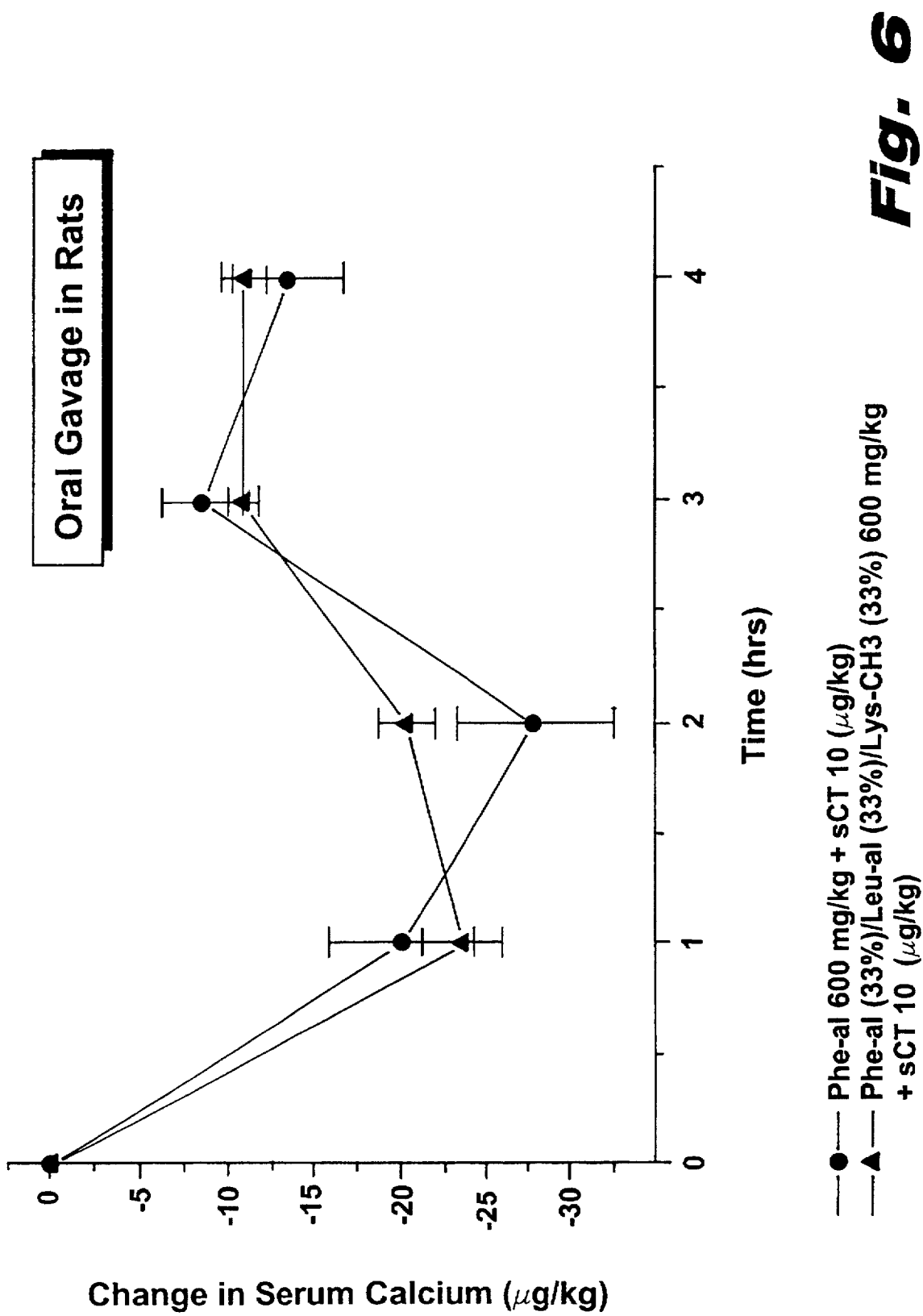

A sample having 600 mg/kg of acetyl-Phe aldehyde and 10 Ag/kg of calcitonin in aqueous ethanol, and 3 µg/kg of calcitonin was prepared. The sample was given to fasted rats as described in Example 7. The results of the test are illustrated in FIG. 6.

Example 13

Figure 7:
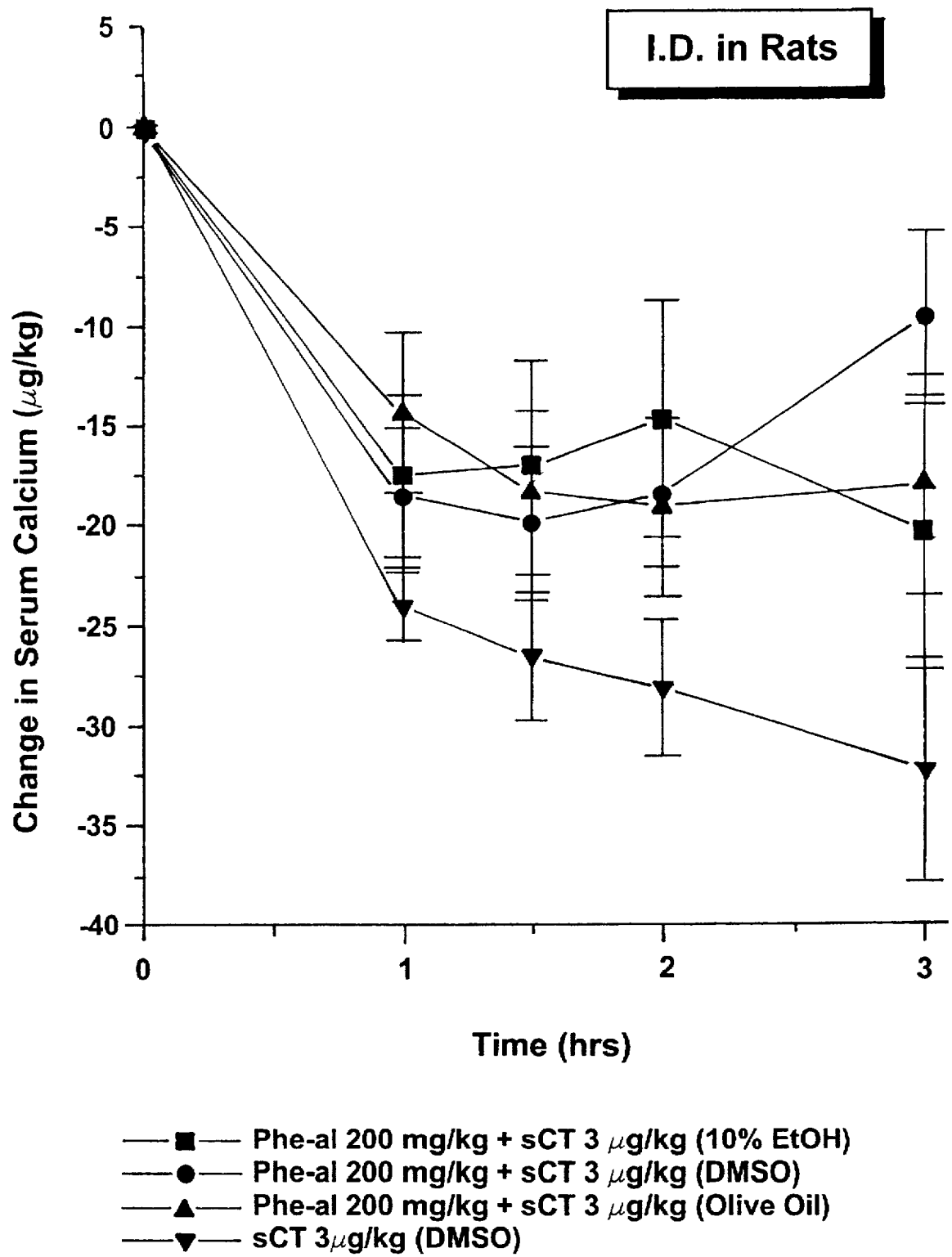

Three samples having 200 mg/kg of acetyl-Phe aldehyde and 3 µg/kg of calcitonin, in aqueous ethanol, dimethyl sulfoxide (DMSO), and olive oil, respectively, were prepared. The samples were given to fasted rats as described in Example 7. The results of the test are illustrated in FIG. 7.

Example 14

Figure 8:
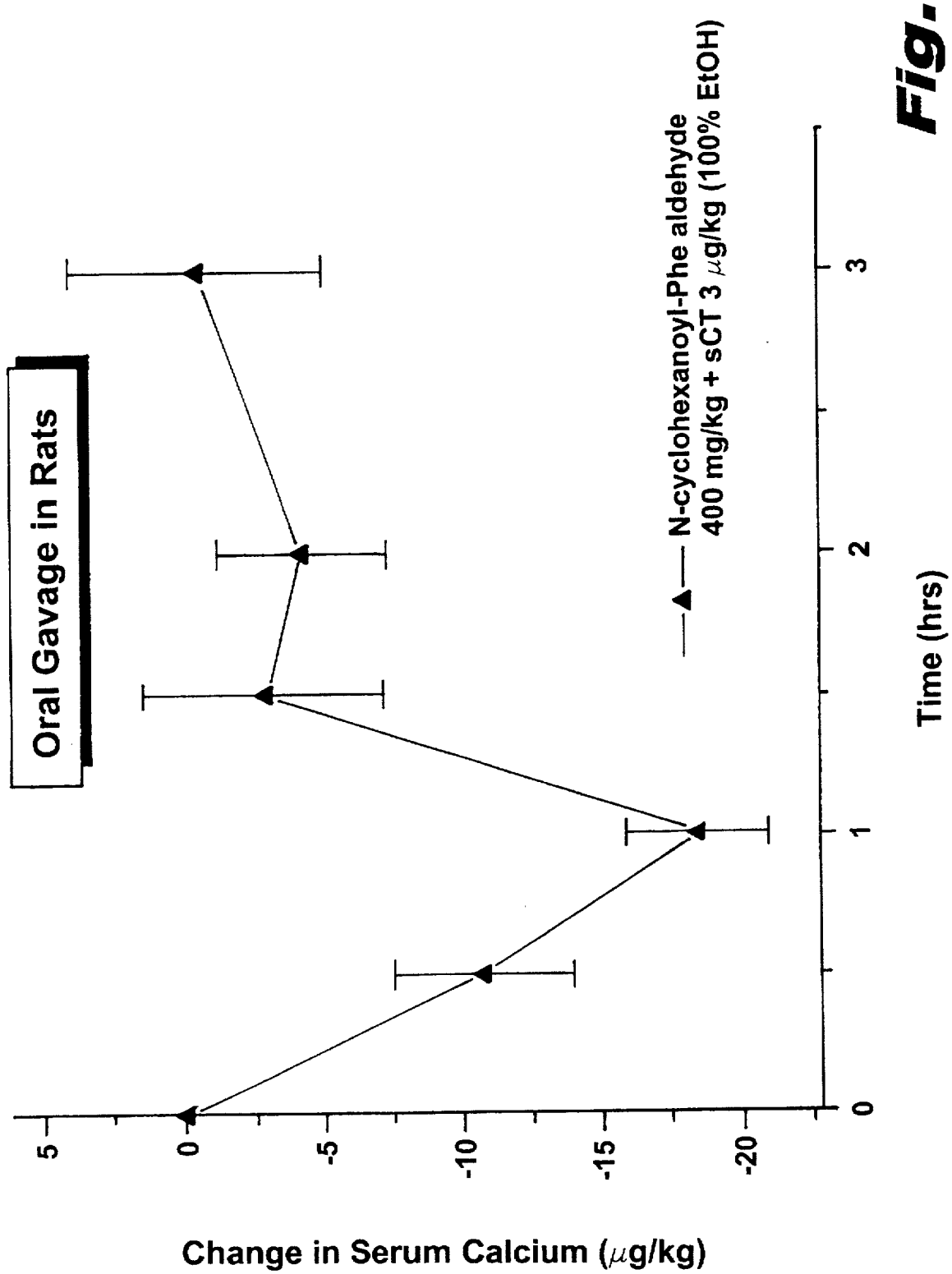

A sample having 400 mg/kg of cyclohexanoyl-Phe aldehyde and 3 µg/kg of calcitonin in aqueous ethanol was prepared. The sample was given to fasted rats as described in Example 7. The results of the test are illustrated in FIG. 8.

As clearly illustrated by the data in the Examples and FIGS. 1–8, the use of compositions of the subject invention show significant advantages for the delivery of biologically active agents.

All patents, applications, and publications mentioned herein are hereby incorporated by reference herein.

Many variations of the present invention will suggest themselves to those skilled in the art in light of the above detailed disclosure. For example, poly (amino acids) which are formed by a bond other than an amide bond, e.g., an ester or an anhydride linkage, may be derivatized and modified for use as carriers in accordance with the present invention. All such modifications are within the full intended scope of the appended claims.

What is claimed is:

1. An oral delivery pharmacological composition comprising:

(A) at least one biologically-active agent; and
(B) at least one carrier comprising
  (a) (i) at least one acylated aldehyde of an amino acid,
    (ii) at least one acylated ketone of an amino acid,
    (iii) at least one acylated aldehyde of a peptide,
    (iv) at least one acylated ketone of a peptide, or
    (v) any combination of (a)(i), (a)(ii), (a)(iii) and (a)(iv);
  (b) (i) carboxymethyl-phenylalanine-leucine,
    (ii) 2-carboxy-3-phenylpropionyl-leucine,
    (iii) 2-benzylsuccinic acid,
    (iv) (phenylsulfonamide) phenylbutyric acid,
    (v) or any combination of (b)(i), (b)(ii), (b)(iii) and (b)(iv); or
  (c) a combination of (a) and (b);

wherein said carrier is in an amount effective for oral delivery of said biologically-active agent.

2. The composition according to claim 1, wherein said biologically-active agent comprises at least one peptide, mucopolysaccharide, carbohydrate, or lipid.

3. The composition according to claim 2, wherein said biologically-active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, vancomycin, desferrioxamine (DFO), and any combination thereof.

4. The composition according to claim 2, wherein said biologically-active agent comprises an interferon, interleukin-II, insulin, heparin, calcitonin, oxytocin, vasopressin, vancomycin, desferrioxamine (DFO) and combinations thereof.

5. The composition according to claim 4, wherein said biologically-active agent comprises calcitonin.

6. The composition according to claim 1, wherein said amino acid is a naturally occurring amino acid.

7. The composition according to claim 1, wherein said amino acid is a synthetic amino acid.

8. The composition according to claim 1, wherein said amino acid is an α-amino acid.

9. The composition according to claim 1, wherein said amino acid is selected from the group consisting of alanine, arginine, asparagine, aspartic acid, citrulline, cysteine, cystine, glutamine, glycine, histidine, isoleucine, leucine, lysine, methionine, ornithine, phenylalanine, phenylglycine, proline, serine, threonine, tryptophan tyrosine, valine, hydroxy proline, γ-carboxyglutamate, O-phosphoserine, β-alanine, α-amino butyric acid, γ-amino butyric acid, α-amino isobutyric acid, ε-amino caproic acid, 7-amino heptanoic acid, β-aspartic acid, γ-glutamic acid, cysteine (ACM), ε-lysine, ε-lysine (A-Fmoc), methionine sulfone, norleucine, norvaline, ornithine, d-ornithine, p-nitro-phenylalanine, hydroxy proline, and thioproline.

10. The composition according to claim 9, wherein said amino acid is selected from the group consisting of arginine, leucine, lysine, phenylalanine, tyrosine, valine, and phenylglycine.

11. The composition according to claim 1, wherein said peptide is selected from the group consisting of a di-peptide, a tri-peptide, a tetra-peptide, or a penta-peptide.

12. The composition according to claim 1, wherein said peptide comprises at least one naturally occurring amino acid.

13. The composition according to claim 1, wherein said peptide comprises at least one synthetic amino acid.

14. The composition according to claim 1, wherein said peptide comprises at least one α-amino acid.

15. The composition according to claim 1, wherein said peptide is formed from one or more amino acids selected from the group consisting of alanine, arginine, asparagine, aspartic acid, citrulline, cysteine, cystine, glutamine, glycine, histidine, isoleucine, leucine, lysine, methionine, ornithine, phenylalanine, phenylglycine, proline, serine, threonine, tryptophan tyrosine, valine, hydroxy proline, γ-carboxyglutamate, O-phosphoserine, β-alanine, α-amino butyric acid, γ-amino butyric acid, α-amino isobutyric acid, ε-amino caproic acid, 7-amino heptanoic acid, β-aspartic acid, γ-glutamic acid, cycteine (ACM), ε-lysine, ε-lysine (A-Fmoc), methionine sulfone, norleucine, norvaline, ornithine, d-ornithine, p-nitro-phenylalanine, hydroxy proline, and thioproline.

16. The composition according to claim 15, wherein said peptide is formed from one or more amino acids selected from the group consisting of arginine, leucine, lysine, phenylalanine, tyrosine, valine, and phenylglycine.

17. The composition according to claim 1, wherein said acylated aldehyde or acylated ketone is acylated by an acylating agent having the formula R—CO—X wherein R is alkyl, cycloalkyl, or aryl, and X is a leaving group.

18. The composition according to claim 17, wherein R is methyl, ethyl, cyclohexane, cyclopentane, phenyl or benzyl.

19. The composition according to claim 17, wherein R—CO is cyclohexyl, carboxyl, or acetyl.

20. A dosage unit form comprising (A) a pharmacological composition according to claim 1; and (B) (a) an excipient, (b) a diluent, (c) a disintegrant, (d) a lubricant, (e) a plasticizer, (f) a colorant, (g) a dosing vehicle, or (h) any combination thereof.

21. A dosage unit form according to claim 20 comprising a tablet, a capsule, or a liquid.

22. A dosage unit form according to claim 20, wherein said dosing vehicle is selected from the group consisting of water, 1,2-propane diol, ethanol or any combination thereof.

23. A method for administering a biologically-active agent to a mammal in need of said agent, said method comprising administering orally to said mammal a composition as defined in claim 1.

24. A method for preparing an oral delivery pharmacological composition, said method comprising mixing:

(A) at least one biologically-active agent;

(B) a carrier comprising (a) (i) at least one acylated aldehyde of an amino acid,
(ii) at least one acylated ketone of an amino acid,
(iii) at least one acylated aldehyde of a peptide,
(iv) at least one acylated ketone of a peptide, or
(v) any combination of (a)(i), (a)(ii), (a)(iii) and (a)(iv);

(b) (i) carboxymethyl-phenylalanine-leucine,
(ii) 2-carboxy-3-phenylpropionyl-leucine,
(iii) 2-benzylsuccinic acid, or
(iv) (phenylsulfonamido) phenylbutyric acid,
(v) or any combination of (b)(i), (b)(ii), (b)(iii) and (b)(iv); or (c) a combination of (a) and (b); and (C) optionally a dosing vehicles;

wherein said carrier is in an amount effective for oral delivery of said biologically-active agent.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
  (A) LENGTH: 4 amino acids
  (B) TYPE: amino acid
  (C) STRANDEDNESS: Not Relevant
  (D) TOPOLOGY: Not Relevant (ii) MOLECULE TYPE: peptide (ix) FEATURE:
  (A) NAME/KEY: Modified-site
  (B) LOCATION: 1
  (D) OTHER INFORMATION: /product="ACETYL-PHENYLALANINE"

(ix) FEATURE:
  (A) NAME/KEY: Modified-site
  (B) LOCATION: 4
  (D) OTHER INFORMATION: /product="ARGININE ALDEHYDE"

(xi) SEQUENCE DESCRIPTION: SEQ ID NO:1:

Phe  Leu  Leu  Arg
1

---

(1) GENERAL INFORMATION:

(i) APPLICANT: Sarubbi, Donald J. Leone-Bay, Andrea Paton, Duncan R.

(ii) TITLE OF INVENTION: ORAL DRUG DELIVERY COMPOSITIONS AND METHODS (iii) NUMBER OF SEQUENCES: 1

(iv) CORRESPONDENCE ADDRESS:
  (A) ADDRESSEE: Darby & Darby, P.C.
  (B) STREET: 805 Third Avenue
  (C) CITY: New York
  (D) STATE: New York
  (E) COUNTRY: USA
  (F) ZIP: 10022

(v) COMPUTER READABLE FORM:
  (A) MEDIUM TYPE: Floppy disk
  (B) COMPUTER: IBM PC compatible
  (C) OPERATING SYSTEM: PC-DOS/MS-DOS
  (D) SOFTWARE: PatentIn Release #1.0, Version #1.30

(vi) CURRENT APPLICATION DATA:
  (A) APPLICATION NUMBER: US 08/205,511
  (B) FILING DATE: 02-MAR-1994
  (C) CLASSIFICATION: 424

(viii) ATTORNEY/AGENT INFORMATION:
  (A) NAME: Robinson, Joseph R.
  (B) REGISTRATION NUMBER: 33,448
  (C) REFERENCE/DOCKET NUMBER: 1946/09323

(ix) TELECOMMUNICATION INFORMATION:
  (A) TELEPHONE: 212-527-7700
  (B) TELEFAX: 212-753-6237
  (C) TELEX: 236687

(2) INFORMATION FOR SEQ ID NO:1:

(i) SEQUENCE CHARACTERISTICS:
  (A) LENGTH: 4 amino acids
  (B) TYPE: amino acid
  (C) STRANDEDNESS: not relevant
  (D) TOPOLOGY: not relevant (ii) MOLECULE TYPE: peptide (ix) FEATURE:
  (A) NAME/KEY: Modified-site
  (B) LOCATION: 1
  (D) OTHER INFORMATION: /product="ACETYL-PHENYLALANINE"

(ix) FEATURE:
  (A) NAME/KEY: Modified-site
  (B) LOCATION: 4
  (D) OTHER INFORMATION:/product="ARGININE ALDEHYDE"

(xi) SEQUENCE DESCRIPTION: SEQ ID NO:1: Phe Leu Leu Arg 1